United States Patent [19]

Komoto et al.

[11] Patent Number: 4,801,607
[45] Date of Patent: Jan. 31, 1989

[54] ANTIVIRAL FURANODITERPENOIDS

[75] Inventors: Shigeo Komoto; Oliver J. McConnell, both of Vero Beach; Sue S. Cross, Ft. Pierce, all of Fla.

[73] Assignee: Harbor Branch Oceanographic Institution, Inc., St. Pierce, Fla.

[21] Appl. No.: 30,727

[22] Filed: Mar. 25, 1987

[51] Int. Cl.$^4$ .................... A61K 31/34; C07D 307/77
[52] U.S. Cl. ..................................... 514/468; 549/457
[58] Field of Search ......................... 549/457; 514/468

[56] References Cited
PUBLICATIONS
Chem. Abstracts, vol. 91, 123895g (1979).

Primary Examiner—John M. Ford
Assistant Examiner—Bernard I. Dentz
Attorney, Agent, or Firm—Carroll F. Palmer

[57] ABSTRACT

This invention relates to antitumor and antiviral furanoditerpenoid compositions, a process of producing the compositions and a method for inhibiting tumors and viruses utilizing the compositions. More particularly, the new compositions are antitumor and antiviral furanoterpenoids which are derived from marine organisms, i.e., the marine sponge Spongia sp.

8 Claims, No Drawings

ANTIVIRAL FURANODITERPENOIDS

FIELD OF THE INVENTION

This invention relates to new cyclic organic compounds which have useful antiviral and antitumor activity. More particularly, this invention relates to new furanoditerpenoid antitumor and antiviral compositions derived from marine organisms, i.e., the marine sponge, Spongia, sp. and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of origin or the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors, new methods and antitumor chemical compositions are needed.

Viral diseases also inflict man, plants, insects, and animals. The prevention and control of viral diseases has important health and economic implications.

Viral diseases contribute to inflictions in humans including common colds, herpes and cancer and the importance of their control is obvious. Also important is the control of viral diseases in animals for economic reasons as well as the ability of such animals to become virus reservoirs or carriers which facilitate the spreading of viral diseases to humans. Viral plant diseases have been known to have a disruptive effect on the cultivation of fruit trees, tobacco, and various vegetables. Insect viral diseases are also of interest because of the insects' ability to transfer viral diseases to humans.

The prevention and control of viral diseases is thus of prime importance to man and considerable research has been devoted to antiviral measures. Certain methods and chemical compositions have been developed which aid in inhibiting, controlling or destroying viruses but additional methods and antiviral chemical compositions are needed.

Marine organisms and particularly marine sponges are a potential source for chemically and biologically interesting molecules of great diversity. Some such molecules derived from sponges are described in Scheuer, P. J. Ed., *Marine Natural Products, Chemical and Biological Perspectives;* Academic Press; New York, 1978–1983; Vol. I-V; Faulkner, D. J. *Natural Products Reports* 1984, Vol. 1, 551–598; and P. Kazlauskas, P. T. Murphy, R. J. Wells, K. Noack, W. F. Oberhansli, and P. Schonholzer, *Aust. J. Chem.*, 32, 867–880 (1979). This article discloses various tetracyclic furanoditerpenes isolated from sponges of the genus Spongia from the Great Barrier Reef in Australia. Also disclosed therein at page 869 and designated as composition 11 is a tetrol which was obtained by reduction of spongiatriol triacetate. No antitumor and antiviral activity is disclosed for these furanoditerpenes. The entire disclosures of these references are hereby incorporated herein by reference.

It has now been found that certain new furanoditerpenoid compositions derived from extracts of the marine sponge, Spongia, sp. possess useful antitumor and antiviral activity. It has also been found by the present inventors that certain of the known spongiadiols described in the above-referenced article of Kazlauskas et al. possess useful antitumor and antiviral activity.

SUMMARY OF THE INVENTION

It is therefore an object of the invention to provide novel compositions which are useful as antiviral and antitumor agents and a process for producing such novel antitumor and antiviral compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described herein, the invention comprises compositions of the general formula (I)

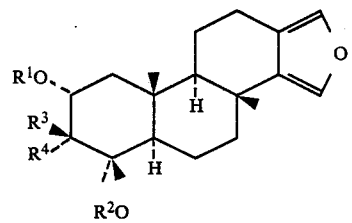

wherein $R^1$ and $R^2$ are the same or different and are a hydrogen, lower alkyl, or lower acyl group; $R^3$ and $R^4$ are together a double bonded oxygen or are the same or different and are single bonded hydrogen or hydroxy groups.

In preferred embodiments of the invention, the composition is substantially pure.

In preferred embodiments of the invention $R^1$ and $R^2$ are a hydrogen or acetyl group.

In more preferred embodiments of the invention, the invention comprises a composition named isospongiadiol and has the formula (II):

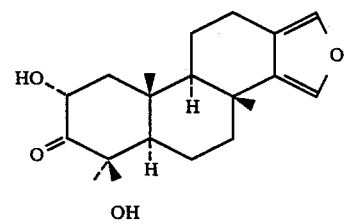

As embodied and fully described herein, the invention also comprises an antiviral and antitumor composition comprising, as active ingredient, an effective antitumor or antiviral amount of one or more compositions according to formulae I or II and a non-toxic pharmaceutically acceptable carrier or diluent.

As embodied and fully described herein, the invention also comprises a process to produce the compositions of formulae I and II. The process comprises the steps of collecting marine sponge Spongia sp; contacting the sponge with at least one suitable organic solvent to obtain an extract comprising a composition according to formula I or II; and isolating a composition according to formula I or II from the extract.

In preferred embodiments of the invention the suitable organic solvent is selected from the group consisting of ethyl acetate, hexanes, heptane, isooctane, methanol, isopropanol, ethanol, toluene, benzene, acetone, diethyl ether, t-butyl-methyl ether, chloroform, 1,2-dichloroethane, dicholoromethane, and combinations thereof.

As embodied and fully described herein, the invention further comprises a method for inhibiting tumors in a host and a therapeutic method for treating cancerous cachexia comprising contacting a tumor with an effective antitumor amount of one or more spongiadiol compositions.

As embodied and fully described herein, the invention further comprises a method for inhibiting viruses comprising contacting a virus with an effective antiviral amount of one or more spongiadiol compositions.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following examples section.

In accordance with the invention novel compositions are provided to achieve the objects in accordance with the purposes of the invention, as embodied and fully described herein, the invention comprises compositions of the general formula (I):

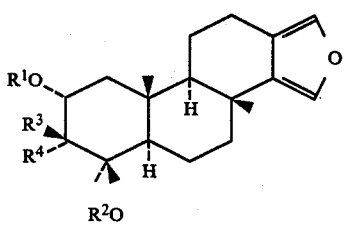

wherein $R^1$, $R^2$, are the same or different and are a hydrogen, lower alkyl, or lower acyl group; $R^3$ and $R^4$ are together a double bonded oxygen or are the same or different and are single bonded hydrogen or hydroxy groups.

In preferred embodiments of the invention the composition is substantially pure.

In preferred embodiments of the invention $R^1$ and $R^2$ are a hydrogen or acetyl group.

In more preferred embodiments of the invention, the invention comprises a composition named isospongiadiol of the formula (II):

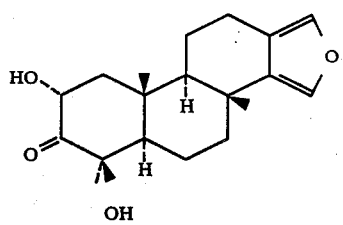

In accordance with the invention, an antitumor composition is provided comprising as active ingredient an effective antitumor amount of one or more of the compositions described above and identified by formulae I or II and a non-toxic pharmaceutically acceptable carrier or diluent. While effective amounts may vary, as conditions in which the antitumor compositions are used vary, a minimal dosage required for in vitro activity is generally between 0.5 and 100 micrograms per milliliter against $10^5$ tumor cells. Useful examples of non-toxic pharmaceutically acceptable carriers or diluents include, but are not limited to, the following: ethanol, methanol, dimethyl sulfoxide and glycerol.

In accordance with the invention, a method for inhibiting tumors in a host is provided comprising contacting a tumor with an antitumor amount of one or more compositions according to formulae I, II or III (described below):

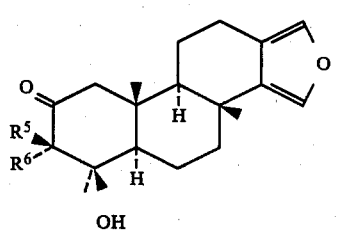

wherein $R^5$ and $R^6$ are the same or different and are a hydrogen or hydroxy. The effectiveness of the compositions of formulae I-III for inhibiting tumors and tumor cells indicates their usefulness for controlling tumors in hosts, including mammals, and for treating cancerous cachexia.

In accordance with the invention, an antiviral composition is provided comprising as active ingredient an effective antiviral amount of one or more of the compositions described above and identified by formula I or II and a non-toxic pharmaceutically acceptable carrier or diluent. While effective amounts may vary, as conditions in which the antiviral compositions are used vary, a minimal dosage required for activity is generally between 50 and 200 micrograms against 100 or less $TCID_{50}$'s of virus. Useful examples of non-toxic pharmaceutically acceptable carriers or diluents include, but are not limited to, the following: methanol, ethanol; dimethyl sulfoxide; and glycerol.

In accordance with the present invention, viral replication is inhibited or atered by a method comprising contacting a virus with an effective antiviral amount of one or more compositions according to formulae I, II or III. The minimal effective amount as stated above is generally from 50 to 200 micrograms against 100 or less TCID$_{50}$'s of virus. The compositions of formulae I–III are active for inhibiting or killing a diverse range of viruses including, but not limited to, the RNA viruses, vesicular stomatitis (herein "VSV"), arenaviruses, coronaviruses, rhinoviruses, influenza viruses and the DNA viruses, herpes simplex-I (herein "HSV-I"), other herpes viruses, adenoviruses, coxsackie viruses, polioviruses and papovaviruses.

The effectiveness of the compositions of the invention for inhibiting virus indicates that the compositions of formulae I–III should also be useful in controlling viral infections in host animals and plants which are caused by a virus which is thus inhibited or destroyed. Viral infections which may be controlled by utilizing compositions of the present invention include, but are not limited to, those caused by those RNA viruses and DNA viruses described above. The invention may also be useful in controlling common viral infections of plants.

In accordance with the invention, a process to produce compositions according to formulae I or II comprises the steps of: collecting the marine sponge Spongia, sp.; contacting the sponge with at least one suitable organic solvent to obtain an organic extract comprising a composition according to formula I or II; and isolating a composition according to formula I or II.

A detailed description and explanation of a preferred embodiment of the process of the invention to produce the compositions according to formula I or II is as follows: the marine sponge Spongia sp. is collected at a depth of 659 feet at Chub Cay, Bahamas. The marine sponge is extracted by steeping with ethyl acetate to obtain an extract which is concentrated to yield a crude residue. The residue is then fractionated by countercurrent chromatography with a suitable solvent system, for example, ethyl acetate/heptane/methanol/water at ratios of 7:4:4:3, respectively.

While ethyl acetate is the presently preferred choice for the extracting solent, other suitable solvents may be substituted. A suitable solvent should be capable of extracting a compound according to any one of formula I or II from other components of the marine sponge. Suitable solvents which may be substituted for ethyl acetate include but are not limited to hexanes, heptane, isooctane, methanol, isopropanol, ethanol, toluene, benzene, acetone, diethyl ether, t-butyl-methyl ether, chloroform, 1,2-dichloroethane, dicholoromethane, and combinations thereof.

Any suitable fractionation and isolation technique may be utilized in accordance with the process of the invention. Suitable fractionation techniques include countercurrent chromotography utilizing a suitable separator-extractor as would be known to those skilled in the art, such as a multilayer coil separator-extractor (ITO). These columns are eluted with suitable eluents such as: heptane; hexanes; ethyl acetate; chloroform; methylene chloride; methanol; acetonitrile; n-propanol; n-butanol; and water; and various combinations and ratios thereof as would be known to those skilled in the art.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

EXAMPLES 1-3

The antitumor and antiviral furanoditerpenoids of the invention were prepared from a marine sponge, Spongia sp., according to the following procedures.

PREPARATION OF COMPOSITIONS 1-3

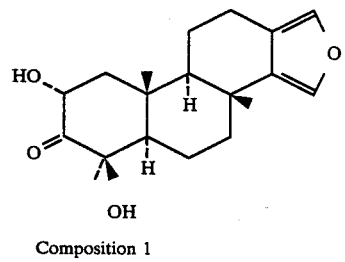

Composition 1

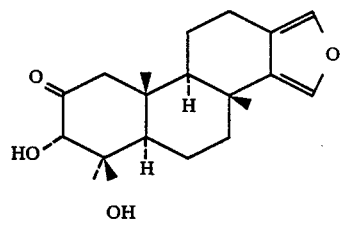

Composition 2

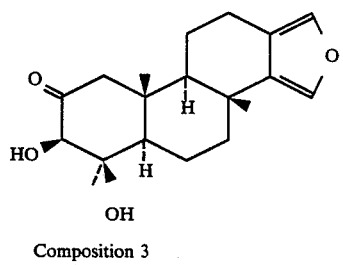

Composition 3

The marine sponge Spongia sp. was collected at a depth of 659 feet at Chubb Cay, Bahamas. An extract of the sponge was prepared by homogenizing the frozen organism and steeping repeatedly with ethyl acetate. 552 milligrams of crude extract was fractionated by repeated multilayer planetary coil countercurrent chromatography (CCC) to yield spongiadiol(2) (39 gm, 0.13% of frozen weight), epispongiadiol(3) (263 mg, 0.87% of frozen weight), and isospongiadiol(1) (61 mg, 0.2% of frozen weight). Isospongiadiol was further purified by recrystallization from MeOH-H$_2$O.

The CCC system employed was the Ito multi-layer coil separator-extractor (P.C., Inc.). The solvent system was EtOAc-heptane-MeOH-H$_2$O (7:4:4:3). The upper phase was used as the mobile phase at a flow rate of 4 ml/min. The instrument was operated at 800 rpm. Twenty-four ml fractions were collected. Isospongiadiol(1) (31 mg) was obtained in fractions 17-19; spongiadiol(2) (29 mg) in fraction 14; and epispongiadiol(3) (195 mg) in fractions 11 and 12. Fractions 1-10 were rechromatographed using the same CCC system to obtain additional epispongiadiol(3) (68 mg, fractions 7'-11'). Fractions 15 and 16 were rechromatographed using the same CCC system to obtain additional spongiadiol (10 mg, fractions 2"-5"), and additional isospongiadiol (30 mg, fractions 7"-14"). Isospongiadiol has structure 1. It is a colorless crystal. The physical and spectral characteristics of 1 are listed below.

mp. 181°-183°

$[\alpha]_D^{20} -50°$ (C=3, $CH_2Cl_2$)

IR: KBr; $cm^{-1}$ 3400, 2950, 2910, 2840, 1700, 1445, 1375, 1260, 1090, 1025.

MS: HREI M/Z=332.1980 (Δ2.5) for $C_{20}H_{28}O_4$

NMR: 360 MHz in $CDCl_3$

Proton: 7.05(d, J=1.5, 1H), 7.03(dd, J=1.5 and 2.7, 1H), 4.62(dd, J=3.1, 6.6 and 12.5, 1H), 4.14(br.d, J=10.8, 1H), 3.66(br.d, J=10.8, 1H), 3.65(br.s, 1H), 2.80(br.dd, J=6.1 and 16.3, 1H), 2.63(dd, J=6.6 and 12.5, 1H), 2.45(dddd, J=1.7, 7.1, 12.1 and 16.3, 1H), 2.16(ddd, J=2.8, 2.8, and 12.7, 1H), 1.30(s, 3H), 1.26(s, 3H), 1.25(s, 3H), 1.87-1.79 (m, 1H), 1.77-1.63 (m, 3H), 1.43-1.37 (m, 2H), 1.30-1.15 (m, 3H).

Carbon 214.19(s) 137.00(d) 136.65(2) 135.05(d), 119.34(s), 69.92(d), 65.58(t), 58.68(d), 55.84(d), 54.57(s), 49.48(t), 41.12(t), 38.00(s), 34.29(s), 26.33(q), 20.47(t), 19.99(t), 19.28(q) 18.76(t), 17.56(q).

Composition 2 (spongiadiol) and composition 3 (epispongiadiol) are described in the above-referenced article to Kazlauskas et al. Compositions 2 and 3 display spectral properties identical to those published in the above-referenced Kazlauskas et al. reference.

ANTITUMOR ACTIVITIES OF THE COMPOSITIONS OF THE INVENTION

The following assay method was utilized to illustrate the antitumor effectiveness of the compositions of formulae I-III, corresponding to composition 1 (isospongiadiol) for example.

P388 MOUSE LEUKEMIA CELL ASSAY

Maintenance of Cell Line

P388 mouse leukemia cells are grown in Dulbecco's minimum essential medium with Earle's salts (MEM) with 10% horse serum, 4 mM glutamine, and 20 ug/ml gentamicin (Biologos, Inc.). Cells are incubated in 10% $CO_2$ and subcultured 2 times per week.

PROCEDURE

1. Add compound to each well of a 24-well plate or tube and allow solvent to evaporate to dryness.
2. Add 2 ml ($1.2 \times 10^5$) cells to each well or tube and mix.
3. Incubate in 10% $CO_2$ at 37° for 48 hours.
4. Read plates with an inverted microscope, scoring activity from 1+ to 4+ as follows: ND (not detectable), >90%; 1+, 75-90%; 2+, 50-74%; 3+, 25-49%; 4+, <25% of control growth. Cell counts are performed on each tube and results are reported as percent of control.

Positive control—Vinblastine or Vincristine in aqueous solution.

HUMAN TUMOR CELL LINE ASSAY

Maintenance of Cell Line

HCT-8 human colon tumor cells are grown in RPM1 1640 medium (GIBCO). A-549 human lung carcinoma cells cells are cultured in Dulbecco medium (Biologos, Inc.). MCF-7, MDA-MB 231 and T47D human breast carcinoma cells are grown in Eagles MEM medium. All media are supplemented with 10% fetal bovine serum and contain 50 μg/ml gentamicin. All human tumor cell lines are incubated in 5% $CO_2$ at 37° and subcultured once a week. The seeding levels are 350,000 MCF-7 cells, 60,000 HCT-8 cells and 300,000 A-549 cells per T25 flask.

PROCEDURE

1. Seed 1 ml of cells (5000 HCT-8, 8000 A549, 12000 MCF-7) into each well of a 24-well plate.
2. Incubate in 5% $CO_2$ for 48 hours.
3. Add compound (50 μg)to each well and incubate for an additional 120 hours.
4. Discard medium and stain with methylene blue (HCT-8) or crystal violet (A549 and MCF-7) for 30 minutes.
5. Compare cell density of drug-treated well with that of the control (no drug added) as follows: ND (not detectable), >90%; 1+, 75-90%; 2+, 50-74%; 3+, 25-49%, 4+, <25% of control growth.

Final Conc. of Vinblastine control (use 2 ul/assay)

| Solution Conc. | Amt added | Final conc. in test |
|---|---|---|
| 50 mg/ml | 2 μl | 50 μg/ml |
| 20 mg/ml | 2 μl | 20 μg/ml |
| 5.0 mg/ml | 2 μl | 5.0 μg/ml |
| 0.5 mg/ml | 2 μl | 0.5 μg/ml |

The results of the above assay are summarized in Table 1, infra.

ANTIVIRAL ACTIVITIES OF THE COMPOSITIONS OF THF INVENTION

The following assay method was utilized to demonstrate the in vitro antiviral effectiveness of the compositions of formulae I-III, corresponding to composition 1, for example.

Antiviral Disc Assay for HSV-1 and VSV

A. Maintenance of Cell Cultures
1. Virus
   a. Both herpes simplex type 1 (HSV-1) and vesicular stomalitis virus (VSV) replicates in the CV-1 cell line. CV-1 is a fibroblast-like cell culture derived from primary African green monkey cells.
2. Growth of CV-1 Cells
   a. Seed 150 $cm^2$ tissue culture flasks each with $10 \times 10^6$ CV-1 cells in 40 ml of EMEM with 10% FBS (growth medium).
   b. Seven days after seeding the flasks cell numbers should be approximately $40-50 \times 10^6$ cells. CV-1 cells have a doubling time of 72 hours based on these numbers.
3. Trypsinization
   a. Aseptically remove the medium b. Rinse cell sheet two times with 10 ml of $Ca^{++}$ and $Mg^{++}$ free Dulbecco's phosphate buffered saline.
c. Add 4.0 ml of trypsin-EDTA mixture.
d. Incubate flask at room temperature with occasional rocking for 5 minutes.
e. Shake flask.
f. Add 10 ml EMEM growth medium and break up cell clumps with pipetting.
g. Count cells.

B. Preparation of plates for viral assays
1. Cell Concentration
a. Dilute the cells with EMEM to $4 \times 10^5$ cells/ml.
b. Seed 24 well trays with 0.5 ml per well. Cell concentration per well is $2 \times 10^5$ cells.
c. Incubate at 37° C. with 5% $CO_2$.
d. The wells can be used over the next several days beginning the day after seeding (preferably 2, 3, or 4).

C. Assay of HSV-1 and VSV in CV-1 cells
1. Infection of CV-1 cells in plates with virus
a. Remove medium from wells.
b. Infect well with at least 25 and no more than 80 plaque forming units (PFU) of virus.
c. Incubate infected cells at 37° C. for 1.0 hour.
d. Pour off supernatant at end of incubation period.
e. Add 0.5 ml of methylcellulose overlay medium (MCO).
   (1) MCO is a maintenance medium without phenol red made with 1% 4000 centipose methylcellulose. FBS is used at 5% level.
2. Drug Evaluation
a. For drug evaluation wet filter paper discs (6 mm diameter) with approximately 0.02 ml of marine extract or test compound.
   (1) Allow solvent to evaporate for 20 to 30 minutes at room temperature.
   (2) Place discs in the well containing CV-1 cells, virus, and MCO.
b. Incubate tissue culture plates for 48 hours at 37° C.
c. After 48 hours place 0.5 ml NRMCO on each well.
   (1) NRMCO is a maintenance overlay medium without phenol red containing 0.1 mg neutral red dye per ml and 2% 15 centipose methylcellulose.
d. Incubate plates at 37° C. and read the following day.
   (1) Antiviral activity should be observed from two parameters. One is actual reduction in the number of plaques and two is the diminution in plaque diameter.
3. Scoring Drug Activity
a. Antiviral activity (AVA) is scored from 0 to +++.
   +++ =complete inhibition of plaque formation
   ++ =partial inhibition
   + =partial inhibition
   0=no protection
b. Cytotoxicity Wells of 24 well tissue culture plates are 16 mm in diameter. Discs are 6 mm in diameter. Zones of cytotoxicity greater than 6 mm are graded from 8 to 16 using only even numbers.
   0=no macroscopic or microscope cytotoxicity
   16=100% toxicity or complete cell destruction
   8, 10, 12, 14=partial cytotoxicity, i.e. diameter of toxic zone including diameter of 6 mm disc.

The results of the above assay are summarized in Table 2.

Antitumor and Antiviral Activity of Isospongiadiol(1), Spongiadiol (2), and Epispongiadiol (3)

TABLE 1

| Antitumor Activity | | | | |
|---|---|---|---|---|
| Mouse P388: | | $IC_{50}$ = 5 µg/ml for (1) | | |
| | | $IC_{50}$ = 0.5 µg/ml for (2) | | |
| | | $IC_{50}$ = 8 µg/ml for (3) | | |
| | | | Composition (1) dose (µg/ml) | |
| Human: | Tumor | Cell line | 50 | 10 | 1 |
| | Colon | HCT-8 | 4+ | 3+ | ND |
| | Lung | A-549 | 4+ | 3+ | ND |
| | Mammary | MDAMB | 4+ | 3+ | ND |

TABLE 2

| Antiviral Activity vs. HSV-1 and VSV virus | | | | |
|---|---|---|---|---|
| | dose (µg/disk) | Cytotoxcity | VSV | Anti-Viral Activity |
| Composition (1) | 20 | 0* | + | +++ |
| | 2 | 0* | − | ++ |
| | 0.2 | 0 | | +/− |
| Compound | (µg/disk) | Cyt. | VSV Activity | HSV-1 Activity |
| Composition (2) | 1 | 0 | +++ | |
| | 0.5 | 0 | ++ | +++ |
| | 0.1 | 0 | − | +/− |
| | 0.01 | 0 | − | − |
| Composition (3) | 20 | 0 | + | |
| | 12.5 | 0 | | ++ |
| | 6.25 | 0 | | + |
| | 2 | 0 | − | |
| | 0.6 | 0 | | − |

*Neutral red staining intensity by microscopic examination is less than the control without drug indicating diffuse toxicity.

Table 1 shows that isospongiadiol (1) spongiadiol (2) and epispongiadiol (3) have good antitumor activity at concentrations of at least 5 to 10 µg/ml against P388 mouse leukemia cells. Isospongiadiol is shown to have good activity against human tumor cell lines in concentrations of at least 10 µg/ml.

It is apparent from the in vitro testing and results reported in Table 1 that the compositions of the invention are effective for inhibiting or destroying tumors and therefore in controlling diseases caused by or related to such tumors in hosts, including mammals, such as cancerous cachexia in fulfillment of the objects of the invention.

Table 2 shows that compositions (1-3) have antiviral activity at concentrations of 0.2 to 20 µg/ml. It is apparant from this in vitro testing that the compositions of the invention are effective for inhibiting viral growth and therefore for controlling viral related diseases in hosts including mammals and plants such as herpes and the common cold, in fulfillment of the objects of the invention.

The scope of the present invention is not limited by the description, examples, and suggested uses herein and modifications can be made without departing from the spirit of the invention. For example, it may be noted that other derivatives of the compositions of example 1 such as halogenated derivatives may possess antitumor and antiviral activity analogous to those preferred embodiments described above. Further, the compositions described herein may have other useful applications such as, for example, analgesic applications. Application of the compositions of the present invention can be accomplished by any suitable therapeutic methods and techniques presently or prospectively known to those skilled in the art. Thus, it is intended that the present invention cover the modifications and variations of this invention provided that they come within the scope of the appended claims and their equivalents.

What is claimed is:

1. A substantially pure compound according to the formula:

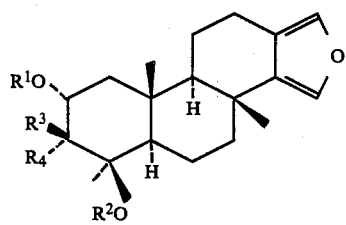

wherein $R^1$ and $R^2$ are the same or different and are a hydrogen, lower alkyl, or lower acyl; and $R^3$ and $R^4$ are together a double bonded oxygen or are the same or different and are single bonded hydrogen or hydroxy groups.

2. A compound according to claim 1 wherein $R^1$ and $R^2$ are the same or different and are a hydrogen or acetyl group.

3. A substantially pure compound according to claim 1 of the formula:

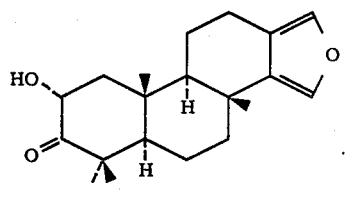

4. A process to produce a compound according to claim 1 comprising the steps of:
    collecting marine sponge Spongia sp.; contacting said sponge with a suitable organic solvent;
    obtaining an extract of the sponge and solvent mixture; and
    isolating by countercurrent chromtography a composition according to claim 1 from the extract.

5. A process to produce a compound according to claim 3 comprising the steps of: collecting marine sponge Spongia sp.; contacting said sponge with a suitable organic solvent; obtaining an extract of the sponge and solvent mixture; and isolating by countercurrent chromatography a composition according to claim 3 from the extract.

6. A pharmaceutical composition comprising, as an active ingredient, an effective antiviral amount of a compound of claim 1 and a non-toxic pharamceutically acceptable carrier or diluent.

7. A pharmaceutical composition comprising, as an active ingredient, an effective antiviral amount of a compound of claim 2 and a non-toxic pharmaceutically acceptable carrier or diluent.

8. A pharmaceutical composition comprising, as active ingredient, an effective antiviral amount of the compound of claim 3 and a non-toxic pharmaceutically acceptable carrier or diluent.

* * * * *

UNITED STATES PATENT AND TRADEMARK OFFICE
CERTIFICATE OF CORRECTION

PATENT NO. : 4,801,607
DATED : January 31, 1989
INVENTOR(S) : Shigeo Komoto, et al.

It is certified that error appears in the above—identified patent and that said Letters Patent is hereby corrected as shown below:

Column 2, lines 35-45; column 3, lines 50-59 and claim 1, change the formula to read:

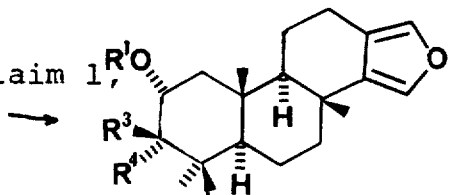

Column 2, lines 60-69; column 4, lines 5-14; column 6, lines 17-25 and claim 3, change the formula to read:

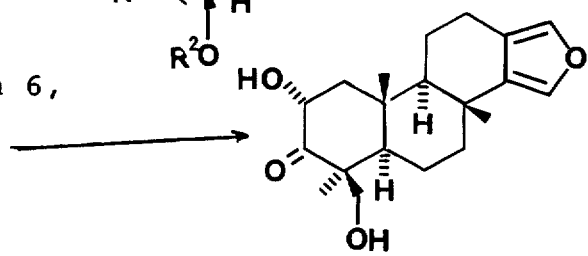

Column 4, lines 35-44, change the formula to read:

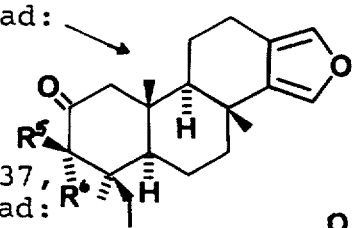

Column 6, lines 29-37, change the formula to read:

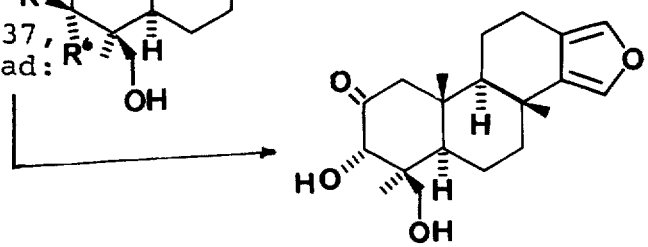

UNITED STATES PATENT AND TRADEMARK OFFICE
CERTIFICATE OF CORRECTION

PATENT NO. : 4,801,607

DATED : January 31, 1989

INVENTOR(S) : Shigeo Komoto, et al

It is certified that error appears in the above-identified patent and that said Letters Patent is hereby corrected as shown below:

Column 6, lines 40-47, change the formula to read:

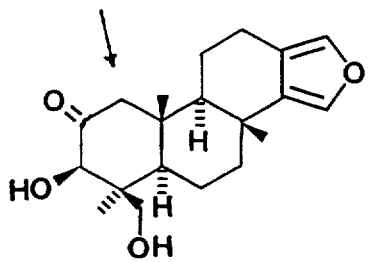

Signed and Sealed this

Tenth Day of April, 1990

Attest:

HARRY F. MANBECK, JR.

*Attesting Officer*    *Commissioner of Patents and Trademarks*